(12) United States Patent
Dillard, III

(10) Patent No.: US 7,799,002 B2
(45) Date of Patent: Sep. 21, 2010

(54) SAFETY SYRINGE

(75) Inventor: John A. B. Dillard, III, Camarillo, CA (US)

(73) Assignee: Protectus Medical Devices, Inc., Camarillo, CA (US)

( * ) Notice: Subject to any disclaimer, the term of this patent is extended or adjusted under 35 U.S.C. 154(b) by 0 days.

(21) Appl. No.: 12/192,014

(22) Filed: Aug. 14, 2008

(65) Prior Publication Data
US 2010/0042053 A1 Feb. 18, 2010

(51) Int. Cl.
*A61M 5/32* (2006.01)
*A61M 5/00* (2006.01)
*F16F 1/00* (2006.01)

(52) U.S. Cl. .................. 604/198; 604/192; 604/110; 604/187; 267/71

(58) Field of Classification Search ......... 604/192–198, 604/110; 267/167
See application file for complete search history.

(56) References Cited

U.S. PATENT DOCUMENTS

| 5,057,086 | A |   | 10/1991 | Dillard, III et al. |         |
|-----------|---|---|---------|---------------------|---------|
| 5,279,584 | A |   | 1/1994  | Dillard, III et al. |         |
| 5,308,332 | A | * | 5/1994  | Dillard et al.      | 604/110 |
| 5,651,480 | A |   | 7/1997  | Piepenstock         |         |
| 5,656,031 | A | * | 8/1997  | Thorne et al.       | 604/110 |
| 2004/0222579 | A1 | * | 11/2004 | Adoline et al. | 267/250 |
| 2007/0060893 | A1 | * | 3/2007  | Mahurkar       | 604/187 |

FOREIGN PATENT DOCUMENTS

| DE | 20 2007 001717 U1 | 7/2007 |
| GB | 732 313 | 6/1955 |
| WO | WO2006/029003 | 3/2006 |

OTHER PUBLICATIONS

EPO International Search Report and Written Opinion of International Application No. PCT/US2009/004526, mailed Dec. 22, 2009.

* cited by examiner

*Primary Examiner*—Kevin C Sirmons
*Assistant Examiner*—Imani Hayman
(74) *Attorney, Agent, or Firm*—Koppel, Patrick, Heybl & Dawson; Michael J. Ram

(57) ABSTRACT

An improved safety hypodermic syringe includes a reciprocal tubular needle sheath disposed on the exterior of the syringe body, a latch mechanism engaging the syringe body and the sheath to latch the sheath in a needle-covering position after delivering contents from the syringe body, and a spring engaging the syringe body and the sheath and expandable to move the sheath to cover the needle point, where the spring is a non-uniform helical spring having multiple 360° turns each turn uniformly spaced from adjacent turns, each 360° turn comprising first and second alternating angled portions, the first of the alternating angled portions being at a first angle to a plane perpendicular to an axis through the center of the helical spring and the second angled portions being at a second lesser angle to the plane perpendicular to the axis.

20 Claims, 9 Drawing Sheets

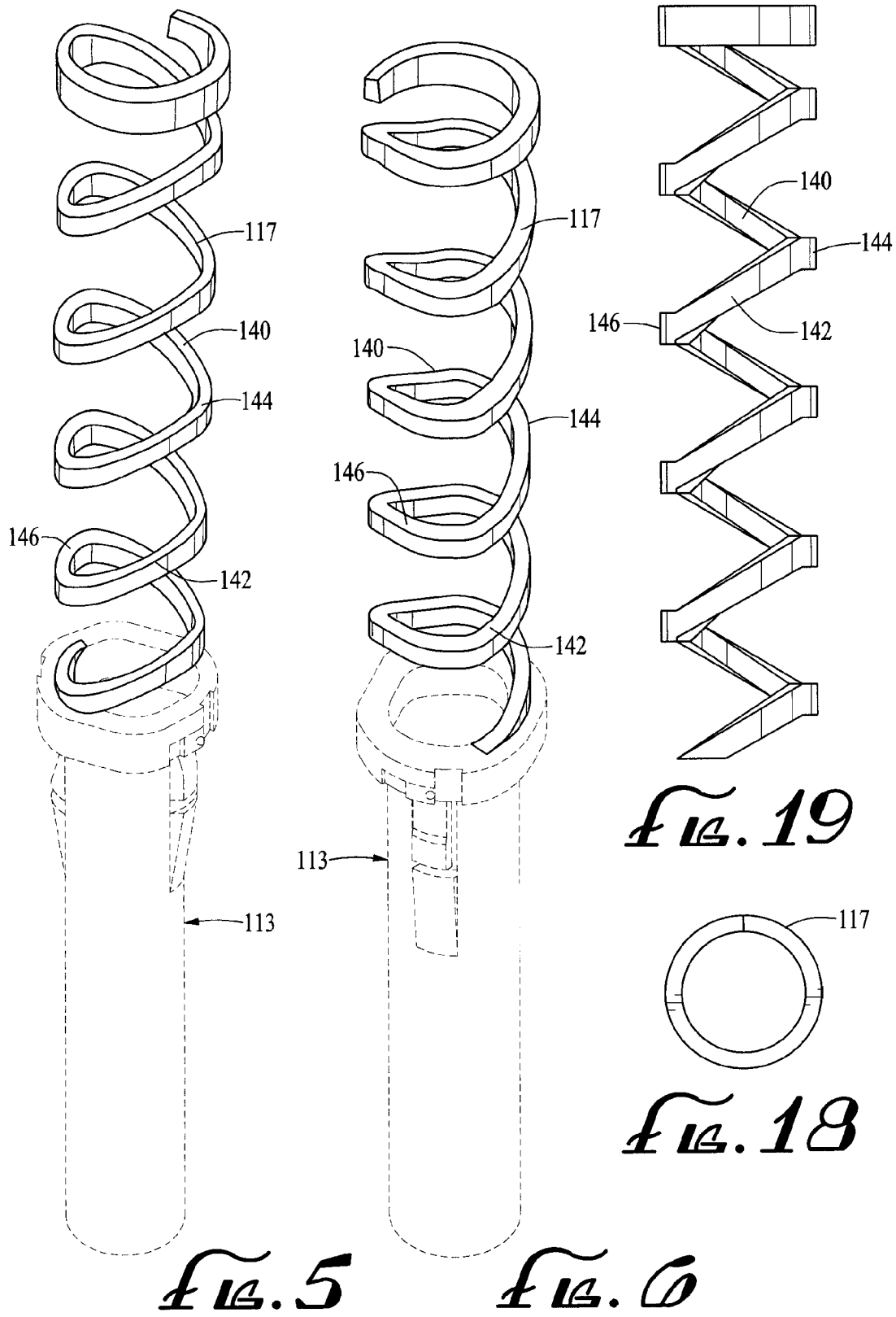

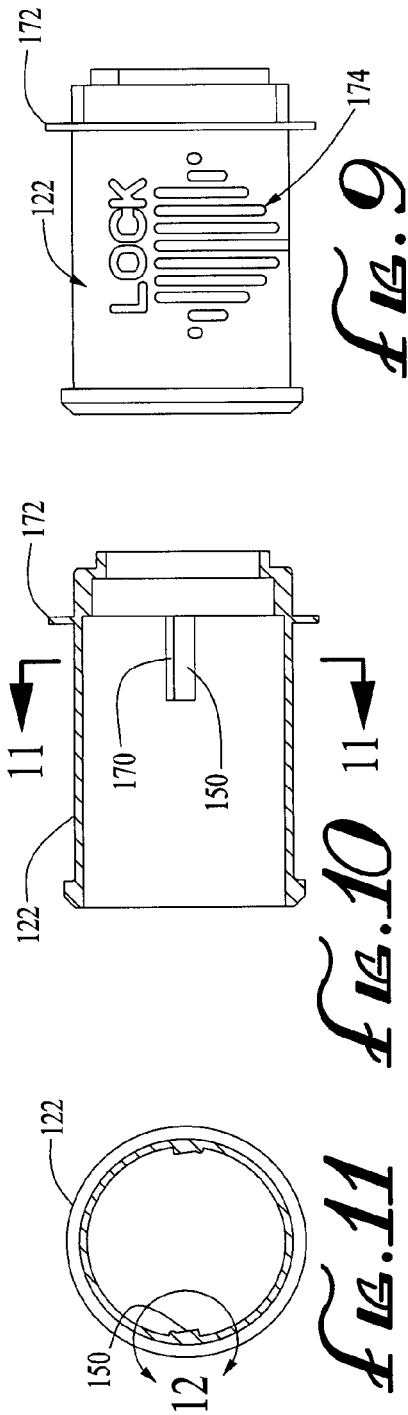
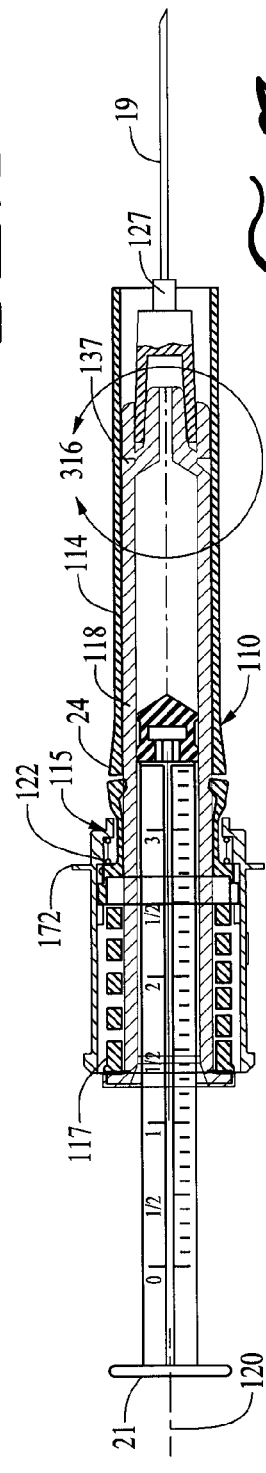
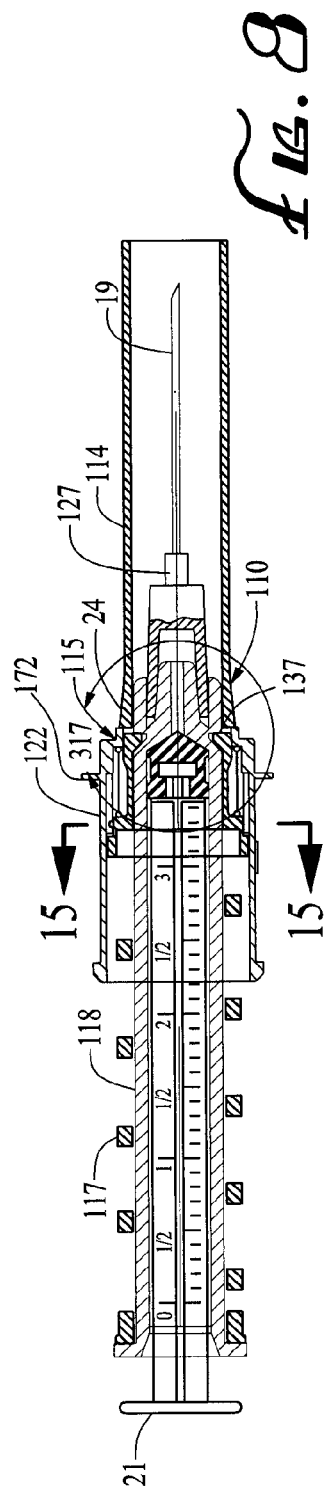

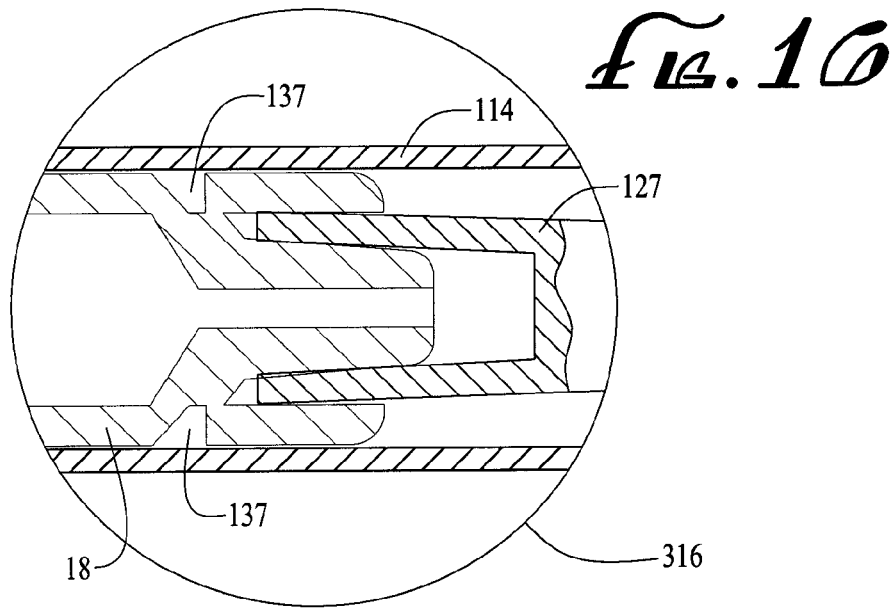
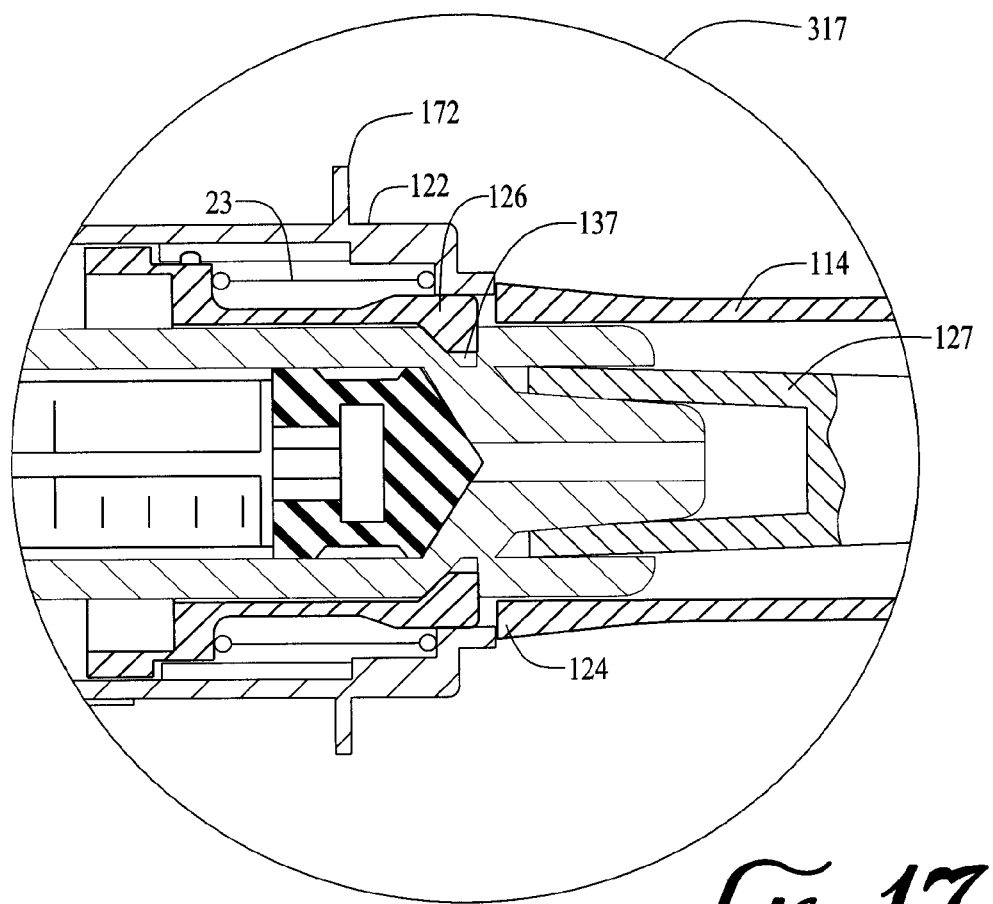

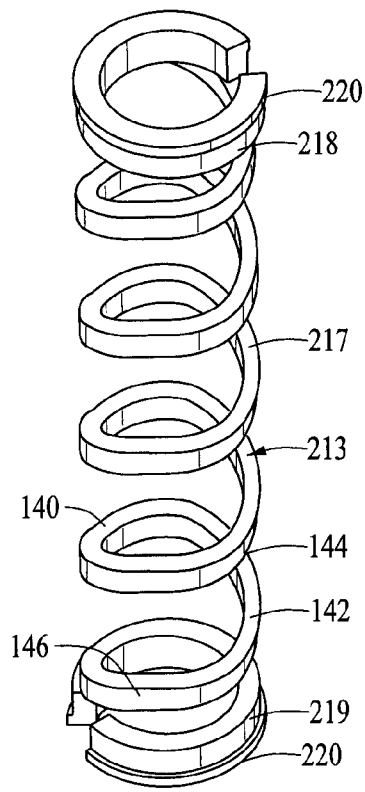
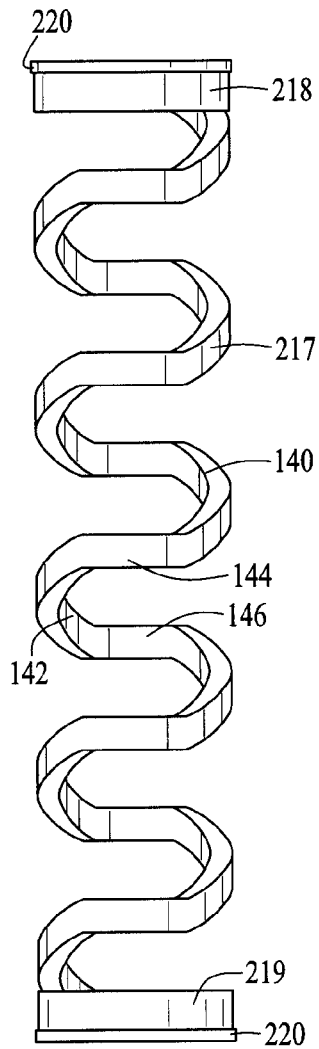
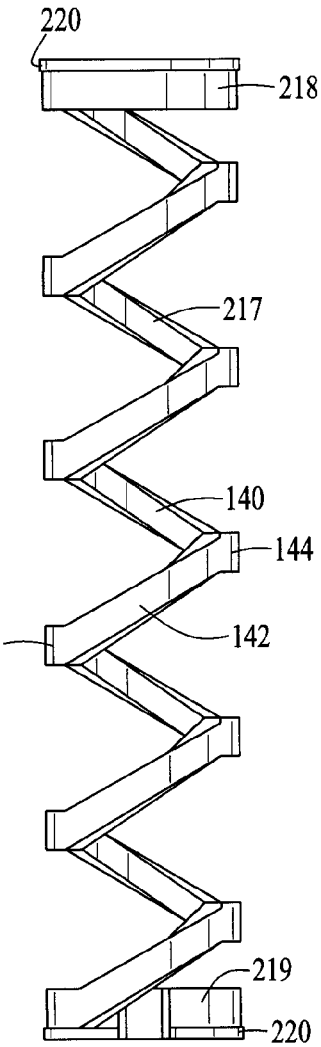
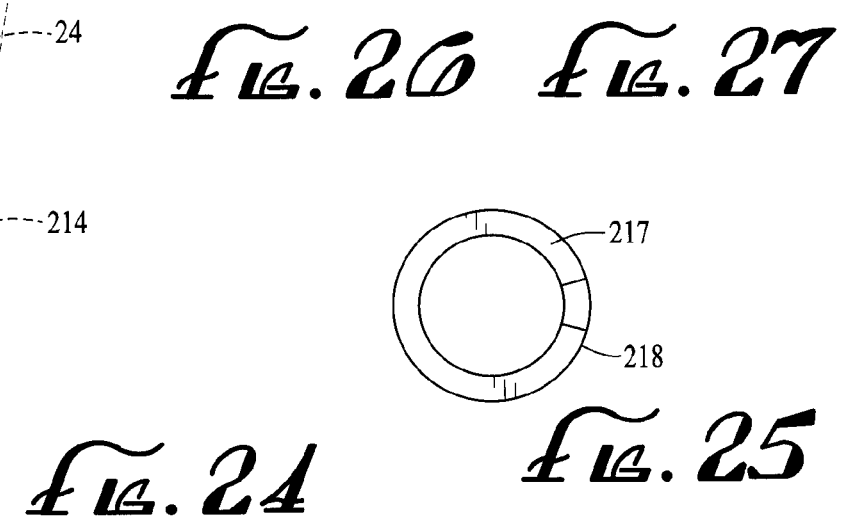
fig. 24   fig. 26   fig. 27
fig. 25

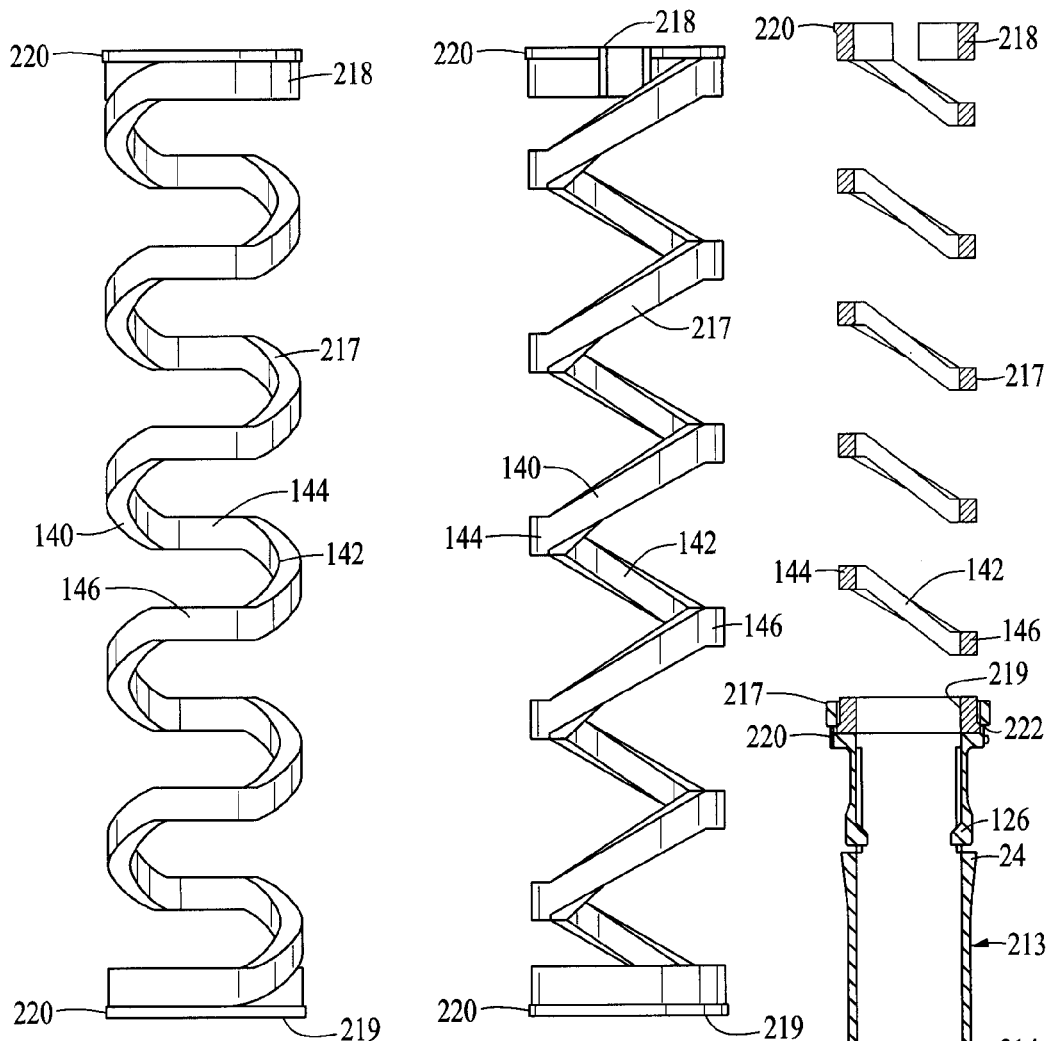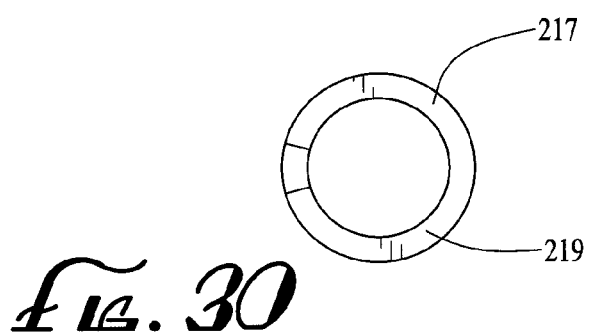

SAFETY SYRINGE

This invention relates to safety syringes and particularly to sliding sheaths moveable to cover needles on hypodermic syringes and has particular reference to the design of the spring and related components, the spring expanding to move the sheath forward, causing the sliding sheath to lock in a protective manner over the needle point or tip. The invention also relates to a unique configuration of a helical spring that has lesser turns and a greater strength when compressed than a comparable diameter prior art helical spring.

BACKGROUND OF THE INVENTION

This invention is an improvement on the sliding sheath mechanism and the spring design for repositioning the sheath of the general type shown in U.S. Pat. No. 5,057,086 granted Oct. 15, 1991, U.S. Pat. No. 5,279,584 granted Jan. 18, 1994 and U.S. Pat. No. 5,308,332 granted May 3, 1994 to John A. B. Dillard III and James A. Orr, said patents incorporated herein in their entirety.

The prior Dillard et al. patents disclose a sliding sheath designed to automatically cover the needle of a syringe if operator loses intentional control, or when the operator finishes injection/use. A ring latch, also referred to as a locking ring mechanism, maintains the sheath in its needle-covering position so that a person cannot accidentally prick himself or another person with the newly contaminated needle. The syringe sheath is propelled to its needle-covering position by a spring, preferably helical, carried on or attached to the exterior of the syringe body. During use of the syringe the operator manually grasps the locking ring or sheath and slides the sheath rearward, which results in compression of the spring to expose the needle point. When the operator has completed injection or use of the syringe, the locking ring or sheath is manually released and the spring propels the sliding sheath forward. If it is operating properly the end of the sheath slides past the point of the needle is then locked in the protecting position. As the sheath nears the forward end of the needle the latch mechanism interacts with the syringe body to latch the sheath in its needle-covering position. Normally, the operator completely releases the sheath, and the spring force moves the sheath forward and the sheath latch mechanism activates to lock the sheath in the needle-covering position However, a problem can arise if the operator allows the spring to gently expand too extend the sheath over the needle. The last stages of spring expansion under this condition has such diminished force that it sometimes does not actuate the latch, and the sheath can then slide rearward under the impact of a blow, exposing the needle point. To alleviate this problem a stronger spring is necessary. However, to increase the strength of the spring in these prior designs the spring requires additional turns, must be thicker in cross-section or must be constructed from a different, stronger material.

A further problem of these prior devices is that in order to provide adequate expansive power, the spring has added turns, the added turns results in a longer collapsed length and, as a result, the collapsed spring length is too great to allow the full length exposure of the needle (i.e., the length from the needle point to the needle hub) to be utilized.

BRIEF DESCRIPTION OF THE INVENTION

The spring can be made stronger by increasing its dimensions or using a different material of construction to get more terminal expansion force. However, this results in an increased size and more costly spring. It has now been discovered that the same material of construction can be employed if the spiral shape is modified to include flat sections. The spring has a significantly greater expansion force and a sufficient terminal force to positively actuate the latch mechanism even when the expansion is gently guided by the fingers of the operator. The locking mechanism has also been modified to provide a more secured locking structure.

DESCRIPTION OF THE DRAWINGS

Referring to the drawings forming an integral part of this specification:

FIG. 5 is a first front perspective view of the sheath spring of FIG. 4 with the sheath shown in dotted lines.

FIG. 6 is a second perspective view of the sheath spring of FIG. 4, taken at a rotation of 90° from the view in FIG. 5, the sheath shown in dotted lines.

FIG. 7 is a cross-sectional view of a safety syringe incorporating features of the invention with the sheath retracted to fully expose the needle to the needle hub.

FIG. 8 is a cross-sectional view of a safety syringe of FIG. 7 with the sheath in its extended and locked position covering the needle.

FIG. 9 is a side view of the locking ring which encloses the latching mechanism.

FIG. 10 is a longitudinal cross-sectional view of the locking ring of FIG. 9.

FIG. 11 is a cross-sectional view of the locking ring of FIG. 9 taken along line 11-11 of FIG. 10.

FIG. 16 is an enlarged view of the circled portion 316 of FIG. 8.

FIG. 17 is an enlarged view of the circled portion 317 of FIG. 7, said view encompassing the same location on the syringe as in FIG. 16, showing both the plunger tip in its forward most position and the sheath in its forward most locked position.

FIG. 18 is a top view of the spring of FIGS. 5 and 6.

FIGS. 19, 20, 21 and 22 are orthogonal views of the spring portion of FIGS. 5 and 6; each successive view rotated 90° from the prior view to provide front, right side, rear and left side views.

FIG. 24 shows a second embodiment of the spring and sheath provided as separate attachable components.

FIG. 25 is a top view of the spring of FIG. 24.

FIGS. 26, 27, 28 and 29 are orthogonal views of the spring portion of FIG. 24; each successive view rotated 90° from the prior view to provide front, right side, rear and left side views.

FIG. 30 is a bottom view of the spring of FIG. 24.

FIG. 31 is a longitudinal cross-sectional view of the embodiment of FIG. 24.

DETAILED DESCRIPTION OF THE DRAWINGS

Figure 1:
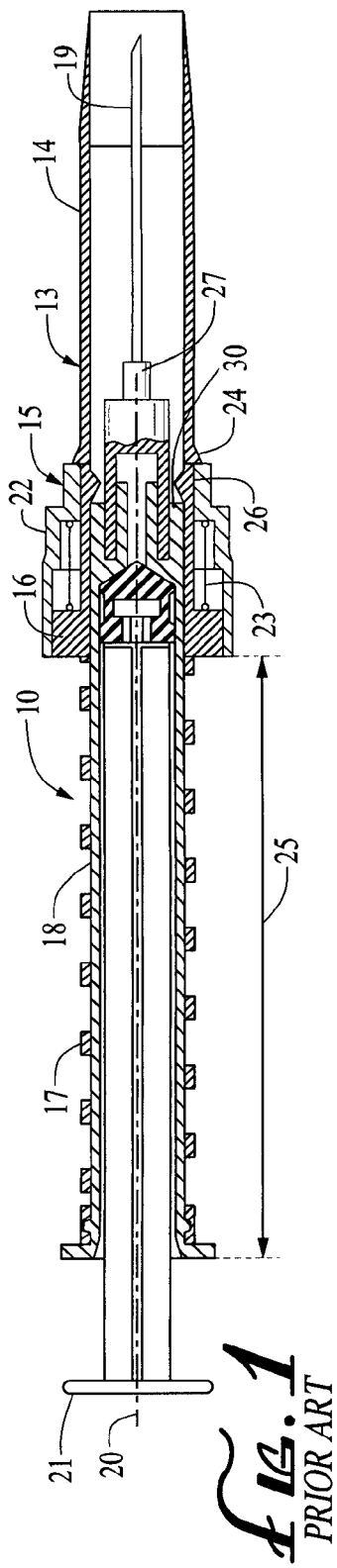
FIG. 1 is a cross-sectional side view of a prior art syringe as set forth in U.S. Pat. No. 5,308,332.
Figure 2:
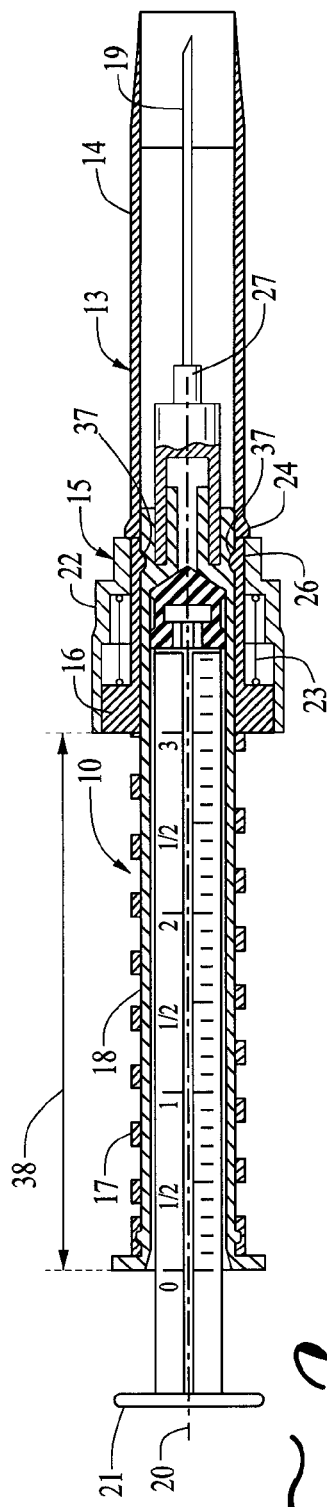
FIG. 2 is a cross-sectional view of a modified prior art form of the syringe of FIG. 1.
Figure 3:
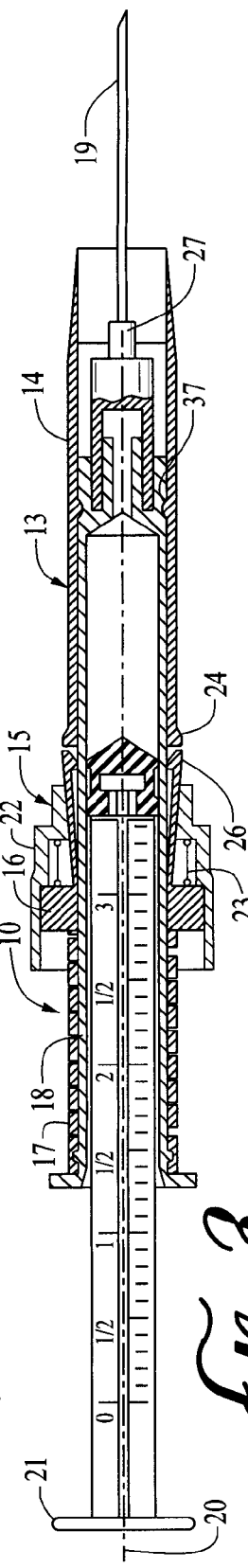
FIG. 3 is a cross-sectional view of the prior art syringe of FIG. 2 with the sheath fully retracted.

Reference is made to the prior art of FIG. 1-3 which is a safety hypodermic syringe 10 shown in U.S. Pat. No. 5,308, 332 incorporated herein in its entirety. In the description of the hypodermic syringe 10, the needle end is referred to as the forward end, movement of a component toward the needle end is referred to as "forward" and movement of a component in a direction away from the forward end is referred to as "rearward". The syringe 10 includes a sheath assembly 13 which includes a reciprocal sheath 14, a latch base 16, and a sheath spring 17. These three parts were of a unitary construction formed of a single piece of material, such as an injection molded plastic. The sheath 14 reciprocates over a hollow syringe body 18 and a hollow needle 19 which is connected to the forward end of the syringe body 18. A manually operated plunger 21 is located within the syringe body. When there is liquid in the syringe body 18, manually pressing the plunger 21 results in the liquid in the syringe body 18 being driven through the hollow needle 19.

The syringe 10 has a longitudinal axis 20 through the syringe body 18 and needle 19. A latch mechanism 15 comprises a reciprocating locking ring 22, which is urged to a forward position by a latch spring 23 which is between the locking ring 22 and over the rear end of the sheath 14, one end of the latch spring 23 bearing against the latch base 16 with the other end bearing against an inner end surface of the locking ring 22. The movement of the locking ring 22 to the forward position is halted by tabs 24 which are integral with but extend outward from the sheath 14.

The latching action on the prior art devices is accomplished by a pair of latch fingers 26 that normally spring radially outward, but are forced radially inward by the forward end of the locking ring 22 when it is moved to the forward position as shown in FIG. 1. These fingers 26 are integrally connected to the sheath 14. When they are forced inwardly as shown in FIG. 1, they extend past and contact the forward end 30 of the hollow syringe body 18, to prevent the sheath 14 from moving rearward. The latch spring 23 normally urges the locking ring 22 forward, which holds the sheath 14 in its extended position as shown in FIG. 1.

After the contents of the syringe 10 are injected and the needle 19 is withdrawn from the puncture site the sheath spring 17 is supposed to drive the sheath 14 forward so that it covers the needle 19 as shown in FIG. 1. The latch spring 23 then moves the locking ring 22 forward, forcing the fingers 26 inward to hold the sheath 14 in its extended or covering position. This construction generally prevents the sheath from being retracted unless considerable force is intentionally applied to the structure to defeat the locking safety features. Therefore, if the syringe 10 contacts other persons, they are protected from injury by the shielded needle 19.

Referring to FIG. 1, the sheath spring 17 is shown in its fully extended condition, the length of the fully extended condition being referred to as the free expansion dimension 25. To use the syringe the sheath 14 is retracted. After delivery of the contents of the syringe 10, the operator releases the locking ring 22 and the sheath spring 17 moves the sheath 14 forward causing the latch base 16 and locking ring 22 to move forward so that the sheath 14 covers the needle 19 as shown. The latch fingers 26 are located forward of the forward end 30 of the syringe body 18. The locking ring 22 is forced to its forward position by the latch spring 23, moving the latch fingers 26 inwardly to the configuration as shown in FIG. 1.

However, in some instances, whether the operator through inadvertence or otherwise allows the sheath spring 17 to only slowly expand or something interferes with the expansion of the sheath spring 17 to its fully expanded dimension 25, experience shows that friction during the last 5% or 10% of the movement will reduce expansion energy of the sheath spring 17 to an extent that the locking function will not properly operate and the latch fingers 26 will not be positioned beyond the forward end 30 of the syringe barrel. In this event the sheath 14 will not move into its locked position and the needle point can be inadvertently exposed, potential injuring the personnel present.

One prior modification was to place a groove 37 at a position rearward of end of the syringe body 18 so that the sheath spring 17 would not have to extend to the same extent to latch. Referring to the prior art device of FIGS. 2 and 3, an annular groove 37 is formed near the forward end of the syringe body 18 to receive the latch fingers 26. The forward movement of the locking ring 22 is limited by raised tab 24, formed from material extending outwardly from the surface of the sheath 14. As a result, the sheath 14 of FIG. 2 must be made longer than the sheath 14 of FIG. 1 to accommodate this change in latching position of the latch fingers 26 and still adequately cover the needle point.

One result of this change is to restrict the expansion of sheath spring 17 to a length referred to as the "Restricted Expansion Dimension" 38. While it was found that this construction improved the locking operation it appears that the spring expansion strength was still not adequate and, as shown in FIG. 3, the number of turns in the spiral spring still prevented adequate retraction of the sheath and fall exposure of the shaft of the needle 19. FIG. 3 shows the device of FIG. 2 in its fully retracted position. Because of the added length of the sheath 14 the full length of the needle 19 is not usable, i.e., the forward end of the needle hub 27 is not exposed.

To avoid the possibility that the sheath does not enter the locked position, another alternative is that the sheath spring 17 can be made stronger by increasing its cross-sectional dimensions or by adding one or more turns to the spiral. However, this solution adds weight and cost to the syringe 10 and increases the compressed length of the spring such that the sheath 14 does not fully retract and restricts insertion of the needle 19 through the puncture site to its full length (i.e., up to the needle hub 27). Applicant has discovered that the necessary force to overcome this non-latching can be obtained by replacing the sheath spring 17 with the unique spring structure shown and described herein below.

It has now been found that prior designs had a problem providing both the ability to withdraw the sheath sufficiently to expose the full length of the needle 19 from its point to the hub 27 and, when the sheath 14 is released, to insure that the needle point is sufficiently covered and the sheath is locked in its forward, needle covering position. This problem has been eliminated by changing the configuration of the spring. The prior art devices such as shown in FIGS. 1-3 included a molded, helical, polycarbonate plastic expansion spring 17 with a uniform spiral configuration. In other words, the coil of the spring forms a three-dimensional curve along a cylindrical surface, such that its angle to a plane perpendicular to the longitudinal axis 20 of the cylinder (i.e., the syringe body 18) is constant. The molded spring comprises a rectangular cross-section (approximately 0.1 in. by 0.35 in) plastic coil with approximately eight turns, each turn being uniformly spaced from the adjacent turn. In its expanded configuration it is approximately 6.3 cm long (the free expanded dimension 25)

and when fully compressed it has a length of approximately 2.8 inches. This allows the sheath to be retracted approximately 3.5 cm. When fully compressed it expands with a force of about 0.9 pounds.

In contrast, a non-uniform spring 117 incorporating features of the invention utilizes a molded, helical, polycarbonate plastic with substantially the same cross-section as the prior art spring 17 and the same polycarbonate material. However, while the turns of the spiral are uniformly spaced from the adjacent turns, the spiral is non-uniform. In other words, the coil of the spring forms a three-dimensional curve along a cylindrical surface, such that its angle to a plane perpendicular to the longitudinal axis 120 of the syringe body 118 is not constant. Referring to FIGS. 4-6, 13, 19-22, 24-29 and 31 and particularly FIG. 19 in a single continuous 360° turn of the spiral, the turn comprises two portions which are at the same angle to a plane perpendicular to the axis of the cylinder (referred to as first and second angled portions 140, 142) and two portions approximately parallel to a plane perpendicular to the axis of the cylinder (referred to as first and second flat portions 144, 146) the angled and flat portions alternating along the length of the spiral. As an example of a suitable construction the non-uniform spiral has a first angled portion 140 for about 120-140° of rotate, a first flat portion 144 for about 40-60° of rotate, a second angled portion 142 for about 120-140° of rotate and a second flat portion 146 for about 40-60° of rotate. This is then repeated for subsequent turns along the length of the non-uniform spiral. The angled portion 140, 142 more preferably constitute 125-135° of rotation, most preferably about 130° of rotation with the flat portions 144, 146 constituting 45-55° of rotation, most preferably about 50° of rotation. However, based on the teachings herein one skilled in the art can adjust the spring tension by adding or reducing the number of turns, changing the angle of rotation occupied by the angle and flat portions, adding additional flat and angled portions within a single turn having only one flat and one angled portion within a single turn, or providing the flat portion at other than approximately parallel to a plane perpendicular to the axis of the syringe body 118, for example, at an angle greater then or less than parallel as long as each successive 360° turn has the same shape to allow complete collapse of each turn against successive turns.

In the embodiment shown the non-uniform spring 117 has approximately 5.5 turns, in its expanded configuration it is approximately 6.6 cm long (the free expanded dimension 25) and when fully compressed it has a length of approximately 2.1 inches. This allows the sheath to be retracted approximately 4.5 cm. When fully compressed it expands to more than three times its compressed length with a force of about 1.3 pounds. The significantly increased expansion force (approximately 45% greater) is a result of the non-uniform spiral shape and the significantly increased expanded length when compared to compressed length (approximately 29%) is a result of the fewer turns in the spring. As a result the sheathed syringe 110 is lighter in weight, requires less polymer to form the syringe, the same length sheath 14 can be withdrawn further to expose a longer needle length allowing better placement into the puncture site, and the increased spring tension allows a more positive locking of the sheath in its protective position after use.

Further, while the design of each 360° turn is described as having angled portions 140,142 and flat portions 144,146, the invention also contemplates alternative portions with different angles to the plane parallel to the longitudinal axis 120. In the embodiment disclosed, the angled portions 140,142 are at an angle of from about 22° to about 45° to the plane, preferably about 33° to the plane and the flat portions 144,146 are parallel to the plane (i.e., at an angle of about 90° to the axis 120). An alternative with two sets of angled portions can, for example, have a first set at the same angle (i.e., 22° to 45°) and a second set at a lesser angle (i.e., 0° to 20°) which may also be at a negative angle (i.e., 0° to 20°). However, the specific disclosed angles are exemplary and not limiting, the distinction being that there is a difference between the angles in the two alternating portions. Irrespective of the combination of angled portions in each 360° turn, each adjacent and successive turn of the helical spring repeats the combination of angled portions.

FIGS. 7 and 8 are a cross sectional views of a sheathed syringe 110 incorporating the above described non-uniform helical spring 117, as evidenced by the spring 117 having far fewer turns then the spring 17 in the prior art devices of FIGS. 1-3. FIG. 7 shows the sheath 114 in its fully retracted position with the needle hub 127 extending beyond the forward end of the retracted sheath 114. FIG. 8 shows the sheath 114 in its fully extended, locked position.

Also shown in FIGS. 7 and 8 are cross sections of the latch mechanism 115. FIGS. 9 and 10 are an enlarged side view and a longitudinal cross-section view respectively of the locking ring 122 of the latching mechanism and FIG. 11 is a view taken along line 11-11 of FIG. 10. Within circled portion 12 of FIG. 11 is one of the two locking tabs 150 on the inner surface of the locking ring 122.

Figure 12:
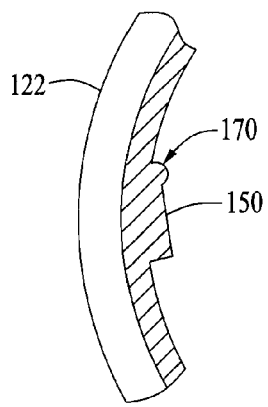
FIG. 12 is an enlarged view of the circled portion of FIG. 11.
Figure 14:
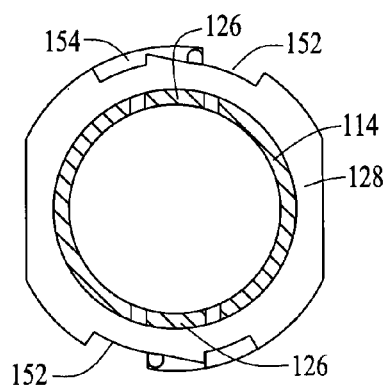
FIG. 14 is a cross-sectional view looking rearward of the sheath and latch base taken along line 14-14 of FIG. 13.
Figures 15A, 15B, 15C:
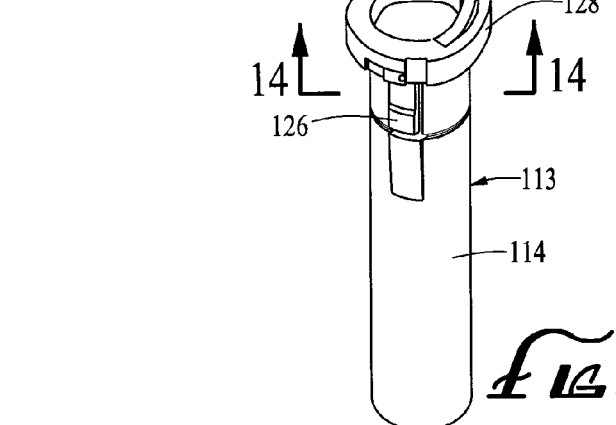
FIGS. 15A, 15B and 15C are cross-sectional views looking rearward of the locking ring and sheath taken along line 15-15 of FIG. 8, with the locking ring rotated relative to the sheath to lock the sheath in its forward position.
Figures 20, 21, 22:
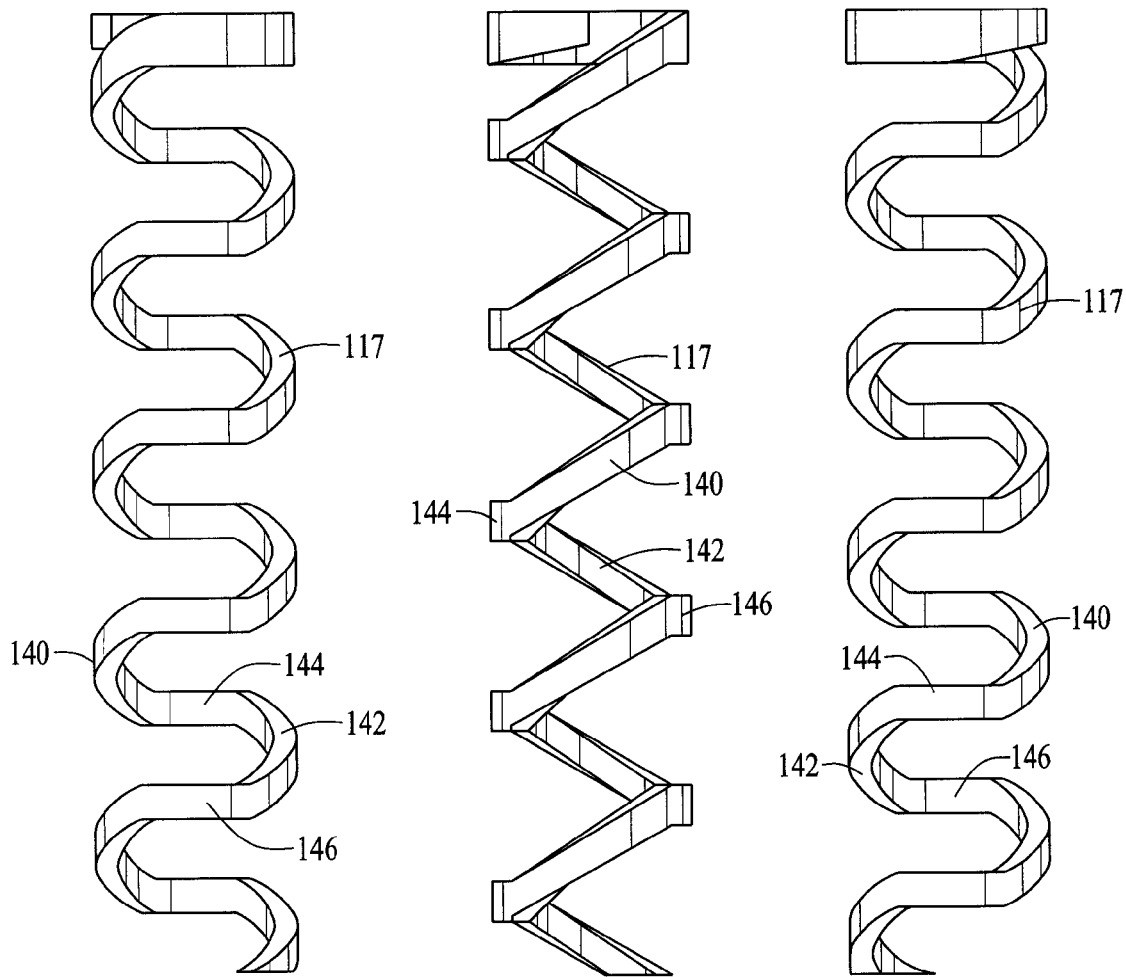
Figure 23:
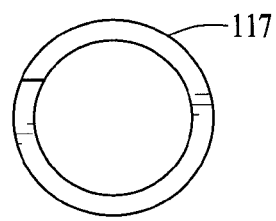
FIG. 23 is a bottom view of the spring of FIGS. 5 and 6.

FIG. 12 is an enlarged view of the circled portion 12 better illustrating one design for the locking tab 150. As described below, the locking tabs 150 interact with grooves, notches or extensions 152 on or in the outer surface of the sheath base 128 so that when the sheath 114 is in its forward position and the locking ring 122 is rotated to its locking position, the latch fingers 126, which are then resting in the groove 137, are locked into that position to prevent inadvertent rearward movement of the sheath 114. To illustrate this locking procedure, reference is made to FIG. 14, which is a cross-section of FIG. 13 at line 14-14 looking rearward and FIGS. 15A, 15B, and 15C taken along line 15-15 of FIG. 8 which are cross-sectional views showing the locking ring 122 in three different rotational orientations. In FIG. 15A, the syringe is shown prior to delivery of its contents with the locking tab 150 resting in a groove 152 on the sheath base 128. To withdraw the sheath 114 for delivery of its contents the user grasps the locking ring 122, the radial extension 172 thereon or sheath 114 and moves it rearward compressing the non-uniform spring 117 and depresses the plunger 21. After delivery of the syringe contents the needle 19 is withdrawn from the injection site, the locking ring 122 or sheath 114 is released and the sheath 114, driven by the spring 117, moves forward to cover the point of the needle 19. The locking ring is then manually rotated, preferably clockwise, so the locking tab 150 moves out of the pass through groove 152 as shown in FIG. 15B over the rib 170 and then into the locking channel 154 as shown in FIG. 15C to place the sheath in a safe (locked) position. The direction of rotation to effect locking can be shown by an arrow 174 molded into the surface of the locking ring. In the safe position the front end of the locking ring 122 is biased forward by the latch spring 23 so that it rests directly over the latch fingers 126 to hold them in the groove 137 to retard or prevent unintended rearward movement of the sheath. To aid in visualizing that the locking ring is moved forward into its locking position over the latch fingers 126, the latching fingers can be colored, for example be provided with a red appearance. If the locking ring is not fully forward the color of the latching fingers 126 is visible forward of the front edge of the locking ring 122. However, when the locking ring is advanced to its forward most position by the latch spring 23 the colored latching fingers are no longer visible, indicating that the sheath is now in its safe mode.

FIG. 16 is an enlarged view of a portion of FIG. 7 enclosed within the circled area 316 to better illustrate the groove 137 on the forward end of the syringe 110 to receive the latch fingers 126. FIG. 17 is an enlarged view of a portion of FIG. 7 enclosed within the circled area 317 to better illustrate the end of the latch fingers 126 resting within the groove 137 on the forward end of the syringe 110 and held within the groove 137 by the front edge of the locking ring 122, now resting against the raised tab 124 on the sheath 114 surface.

Figure 4:
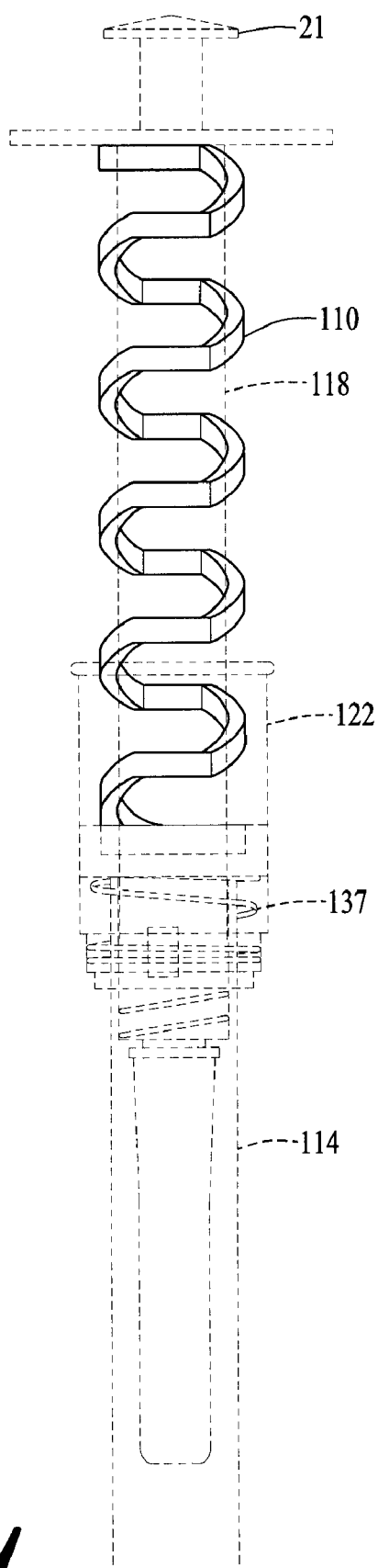
FIG. 4 is a front view of a sheath spring incorporating features of the invention, other syringe components being shown in dotted lines.
Figure 13:
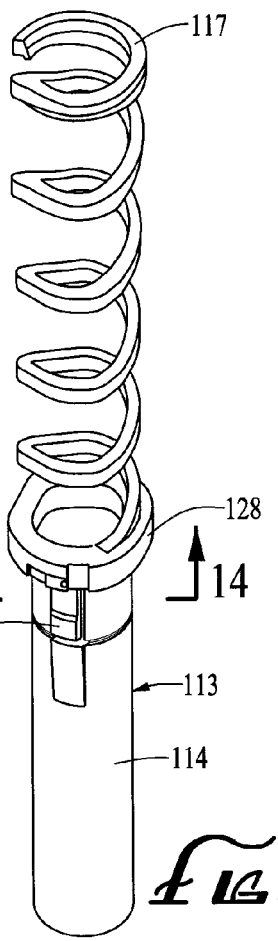
FIG. 13 is a front perspective view of a one piece spring and sheath assembly incorporating features of the invention.

FIG. 13 illustrates a first embodiment of the sheath assembly 113 wherein the non-uniform helical spring 117 is integral with the sheath 114. FIGS. 4, 5 and 6 shows the same embodiment with the sheath and other portions of the safety syringes showed in the dotted lines. FIGS. 18-23 show several different views of the non-uniform spring portion 217 of the sheath assembly 213. In an alternative embodiment of the sheath assembly 213 the non-uniform helical spring 217 can be fabricated separate from the sheath 214 and the two components joined by known plastic joining techniques. FIGS. 24-32 show several different views of the non-uniform helical spring 217 as a separate component from the sheath 214. FIG. 32 is a cutaway side view showing the non-uniform helical spring 217 attached to the sheath 214. A preferred method of joining the spring 217 with the sheath 214 is to form the spring with flat top and bottom ends 218, 219, each end having an enlarged circumferential rim 220 on each of the flat ends 218, 219. The inner surface of the top end of the sheath 214 has a rim-receiving groove 222 so that the pieces can be snapped together. Examples of other joining techniques include, but are not limited to, adhesive or solvent bonding, heat bonding, tack welding, compression assembly and laser bonding.

The safety syringe and the unique non-uniform helical spring have been described with respect to the presently preferred embodiments. Various modifications and improvements will be apparent to those skilled in the art. All such variations, modifications, changes, and improvements that come within the true spirit and scope of the invention are included within the scope of the attached claims.

I claim:

1. An improved safety hypodermic syringe having:
   a) a hollow tubular syringe body,
   b) a hollow needle communicating with the hollow of the syringe body,
   c) a reciprocal tubular needle sheath disposed on the exterior of the syringe body,
   d) a spring engaging the syringe body and the sheath and expandable to move the sheath to cover the needle point, and
   e) a latch mechanism engaging the syringe body and the sheath to latch the sheath in a needle-covering position after delivering contents from the syringe body,
   wherein the improvement comprises a non-uniform helical spring having multiple 360° turns each turn uniformly spaced from adjacent turns, each 360° turn comprising alternating angled portions and flat portions, the angled portions being at an angle to a plane perpendicular to an axis through the center of the helical spring and the flat portions being substantially parallel to the plane perpendicular to the axis.

2. The improved safety hypodermic syringe of claim 1 wherein each 360° turn of the helical spring has a first and second angled portion alternating with a first and second flat portion.

3. The improved safety hypodermic syringe of claim 1 wherein the helical spring comprises five to six 360° turns.

4. The improved safety hypodermic syringe of claim 3 wherein the helical spring when fully compressed has a length of about 2.1 cm and an expanded length of about 6.6 cm.

5. The improved safety hypodermic syringe of claim 3 wherein the spring when fully compressed has an expansion force of about 1.3 pounds.

6. The improved safety hypodermic syringe of claim 3 wherein the fully compressed spring when released expands to more than 3 times its compressed length.

7. The improved safety syringe of claim 2 wherein the spring and the sheath comprise a unitary component.

8. The improved safety syringe of claim 7 wherein the spring and sheath are separate components joined to form a unitary component.

9. The improved safety hypodermic syringe of claim 1 wherein the latch mechanism comprises a rotatable locking ring with an internal extension configured to engage with a groove on the base of the sheath so as to secure latching fingers integral with the sheath into a groove on the syringe body adjacent a hub end of the hollow needle.

10. A helical compression/expansion spring comprising a non-uniform helical spring having multiple 360° turns each turn uniformly spaced from adjacent turns, each 360° turn comprising alternating angled portions and flat portions, the angled portions being at an angle to a plane perpendicular to an axis through the center of the helical spring and the flat portions being substantially parallel to the plane perpendicular to the axis.

11. The helical compression/expansion spring of claim 10 wherein each 360° turn of the helical spring has a first and second angled portion alternating with a first and second flat portion.

12. The helical compression/expansion spring of claim 11 wherein the helical spring comprises five to six 360° turns.

13. The helical compression/expansion spring of claim 12 wherein the helical spring when fully compressed has a length of about 2.1 cm and an expanded length of about 6.6 cm.

14. The helical compression/expansion spring of claim 12 wherein the spring when fully compressed has an expansion force of about 1.3 pounds.

15. The helical compression/expansion spring of claim 12 wherein the fully compressed spring when released expands to more than 3 times its compressed length.

16. The improved safety hypodermic syringe of claim 1 wherein the latch mechanism includes a locking ring in surrounding relationship to the sheath and the syringe, the locking ring having a longitudinal rib on an inside surface thereof, said rib interacting with a pass-through groove and a locking channel on a base of the sheath such that the locking ring is positioned over latching fingers integral with the sheath surface to hold the latching fingers in a groove in the syringe surface rearward of the needle hub to prevent movement of the sheath once locked in the needle-covering position.

17. The improved safety hypodermic syringe of claim 16 wherein locking ring includes a radially extended edge on a forward outer surface thereof for grasping the locking ring for retraction of the sheath.

18. The improved safety hypodermic syringe of claim 16 wherein the latching fingers are colored to aid in visualizing that the sheath is locked in the needle-covering position.

19. The improved safety hypodermic syringe of claim 16 wherein the locking ring includes an arrow on the surface thereof to indicate the radial direction to turn the locking ring to permanently lock the sheath in its needle-covering position.

20. A helical compression/expansion spring comprising a non-uniform helical spring having multiple 360° turns each turn uniformly spaced from adjacent turns, each 360° turn comprising alternating first angled portions and second angled portions, the first angled portions being at a first angle to a plane perpendicular to an axis through the center of the helical spring and the second angled portions being at a second angle to the plane perpendicular to the axis, the first angle and the second angle being different.

* * * * *

UNITED STATES PATENT AND TRADEMARK OFFICE
CERTIFICATE OF CORRECTION

| | | |
|---|---|---|
| PATENT NO. | : 7,799,002 B2 | Page 1 of 1 |
| APPLICATION NO. | : 12/192014 | |
| DATED | : September 21, 2010 | |
| INVENTOR(S) | : John A. B. Dillard, III | |

It is certified that error appears in the above-identified patent and that said Letters Patent is hereby corrected as shown below:

Column 7, Lines 22 & 24, "32" should be --31--

Signed and Sealed this
Eighteenth Day of October, 2011

David J. Kappos
*Director of the United States Patent and Trademark Office*